United States Patent [19]

Higashii et al.

[11] Patent Number: 5,274,168

[45] Date of Patent: Dec. 28, 1993

[54] OPTICALLY ACTIVE BENZENE DERIVATIVES, PROCESS FOR PRODUCING THE SAME AND LIQUID-CRYSTALLINE SUBSTANCES CONTAINING SAID DERIVATIVES AS ACTIVE INGREDIENT AND OPTICAL SWITCHING ELEMENTS

[75] Inventors: Takayuki Higashii, Kishiwada; Masayoshi Minai, Moriyama, both of Japan

[73] Assignee: Sumitomo Chemical Company, Limited, Osaka, Japan

[21] Appl. No.: 986,871

[22] Filed: Dec. 4, 1992

Related U.S. Application Data

[60] Continuation of Ser. No. 589,500, Nov. 9, 1990, abandoned, which is a division of Ser. No. 170,409, Mar. 18, 1988, Pat. No. 5,002,693.

[30] Foreign Application Priority Data

| Mar. 23, 1987 | [JP] | Japan | 62-69485 |
| May 27, 1987 | [JP] | Japan | 62-132600 |
| Jul. 7, 1987 | [JP] | Japan | 62-170030 |

[51] Int. Cl.$^5$ ............ C07C 69/76; C07C 41/00
[52] U.S. Cl. ............ 560/55; 560/59; 560/60; 560/73; 568/631; 568/643; 568/644
[58] Field of Search ............ 560/59, 60, 64; 568/631, 643, 644

[56] References Cited

U.S. PATENT DOCUMENTS

| 4,668,427 | 5/1987 | Saito et al. | 252/299.66 |
| 4,709,030 | 11/1987 | Petrzilka et al. | 560/64 |
| 4,827,052 | 5/1989 | Ohno et al. | 568/812 |
| 4,882,084 | 11/1989 | Ohno et al. | 252/299.66 |

FOREIGN PATENT DOCUMENTS

| 0175591 | 3/1986 | European Pat. Off. |
| 0231853 | 8/1987 | European Pat. Off. |
| 255219 | 2/1988 | European Pat. Off. |
| 0257457 | 3/1988 | European Pat. Off. |
| 270243 | 6/1988 | European Pat. Off. |
| 270244 | 6/1988 | European Pat. Off. |
| 59-219251 | 12/1984 | Japan . |
| 60-149547 | 8/1985 | Japan . |
| 61-43 | 1/1986 | Japan . |
| 61-22051 | 1/1986 | Japan . |
| 61-63633 | 4/1986 | Japan . |
| 61-165350 | 7/1986 | Japan . |
| 61-210056 | 9/1986 | Japan . |
| 62-198647 | 9/1987 | Japan . |
| 63-172788 | 7/1988 | Japan . |
| 8705012 | 8/1987 | PCT Int'l Appl. . |
| 8705018 | 8/1987 | PCT Int'l Appl. . |

OTHER PUBLICATIONS

Bellus et al, "Photorearrangement and photodegradation of Poly(4–benzoyloxystyrene)" *Journal of Polymer Science*, Part C(PT2), pp. 629–643 (1967).–Abstract.
Mol. Cryst. Liq. Cryst. 48, (1978) pp. 37–52.
Bouquet et al, Synthetic Comm. 15 (13), pp. 1153–1157 (1985).

*Primary Examiner*—Jose' G. Dees
*Assistant Examiner*—Keith MacMillan
*Attorney, Agent, or Firm*—Stevens, Davis, Miller & Mosher

[57] ABSTRACT

Disclosed are novel active benzene derivatives represented by the general formula (I):

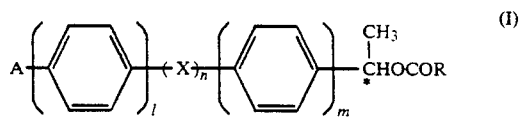

(wherein X represents —COO—, —OCO—, —CH$_2$O— or —OCH$_2$—; A represents a hydrogen atom, a halogen atom or an alkyl or alkoxyl group having 1 to 20 carbon atoms; R represents an alkyl group having 1 to 20 carbon atoms; l and m each represents a number of 1 or 2, n represents a number of 0 or 1, but when n is 0 the sum of l and m is 3 or less; and * indicates asymmetric carbon atom), a process for producing the same, liquid-crystalline substances containing said derivatives as active ingredient, and optical switching elements utilizing the liquid crystal compositions containing said liquid-crystalline substances.

1 Claim, No Drawings

OPTICALLY ACTIVE BENZENE DERIVATIVES, PROCESS FOR PRODUCING THE SAME AND LIQUID-CRYSTALLINE SUBSTANCES CONTAINING SAID DERIVATIVES AS ACTIVE INGREDIENT AND OPTICAL SWITCHING ELEMENTS

This application is a continuation of application Ser. No. 07/589,500, filed Nov. 9, 1990, now abandoned which in turn is a division of application Ser. No. 07/170,409, filed Mar. 18, 1988, now U.S. Pat. No. 5,002,693.

BACKGROUND OF THE INVENTION

1. Field of the Invention

This invention relates to the optically active benzene derivatives represented by the general formula (I):

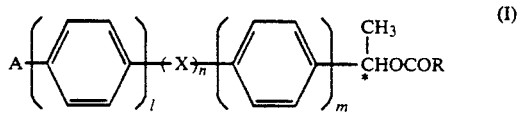

(wherein X represents —COO—, —OCO—, $CH_2O$— or —$OCH_2$—; A represents a hydrogen atom, a halogen atom or an alkyl or alkoxyl group having 1 to 20 carbon atoms; R represents an alkyl group having 1 to 20 carbon atoms; l and m each represents a number of 1 or 2, n represents a number of 0 or 1, but when is 0 the sum of l and m is 3 or less; and * indicates asymmetric carbon atom), a process for producing the same, liquid-crystalline substances containing said derivatives as active ingredient, and optical switching elements utilizing the liquid crystal compositions containing said liquid-crystalline substances.

The term "liquid-crystalline substances" is used in this specification to refer to the liquid-crystalline substances of the broad sense, including those which may not have been confirmed to take a liquid crystal phase per se but can be utilized effectively as a liquid crystal composition.

2. Prior Art

Image display devices using liquid crystal are now practically used in various fields. Twinsted nematic type liquid crystal display is known as one of these display systems. This display system has the advantages that its power consumption is low and it is soft to the eye because of the light-receiving type (the display panel itself is not luminous). Display by this system, however, is not always satisfactory in the aspect of response speed.

As a system which is capable of high speed responses, a display device utilizing the optical switching performance of ferroelectric liquid crystal has been proposed (Applied Physics Letters, 36, 899 (1980)) and is attracting attention.

In view of its molecular configuration, ferroelectric liquid crystal is considered to belong to the type of liquid crystal having chiral smectic C phase (hereinafter referred to as $S_C{}^*$ phase) or chiral smectic H phase ($S_H{}^*$ phase). With its high speed response characteristics, such ferroelectric liquid crystal is expected to find its use not only for display devices such as liquid crystal televisions but also as materials for electronic elements such as optical printer head, photo-Fourier transformation element, etc.

Such known liquid crystal compounds, however, had problems in practical use such as poor stability and were also unsatisfactory in response characteristics, etc., because of small spontaneous polarization. Also, even those compounds which show a high tendency of spontaneous polarization had problem in stability as they possessed halogen atoms in the molecular, and thus they could not be accepted as practical liquid crystal compounds.

In view of the above, the present inventors have made studies for developing a liquid crystal compound which can be widely applied to various types of display systems such as mentioned above, and as a result they found out novel optically active benzene derivatives and achieved the present invention.

SUMMARY OF THE INVENTION

The present invention provides the optically active benzene derivatives represented by the above-described general formula (I). Such optically active benzene derivatives have been unknown in the prior art and disclosed for the first time by the present inventors. These novel compounds can be produced, for instance, by reacting the optical active alcohol compounds represented by the formula (II):

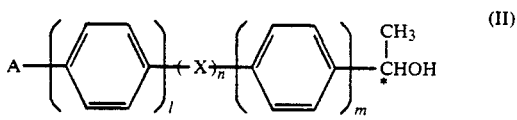

(wherein X, A, l, m, n and * represent the same as defined above) with aliphatic carboxylic acids or acid anhydrides or acid halides thereof (these being hereinafter referred to generically as aliphatic carboxylic acids) represented by the formula (III):

(wherein R is as defined above).

DETAILED DESCRIPTION OF THE INVENTION

The optical active alcohol compounds (II) used as starting material in the above reaction can be obtained by subjecting dl-esters of the formula (IV):

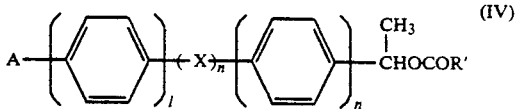

(wherein A, X, l, m and n are as defined above, and R' represents a lower alkyl group) to asymmetric hydrolysis by using an esterase which has the ability to hydrolyze only one of the enantiomers of said esters.

The dl-esters (IV) used in the above reaction can be obtained by acylating the dl-alcohols represented by the formula (V):

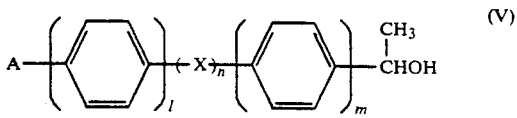

(wherein A, X, l, m and n are as defined above) by reacting them with lower alkylcarboxylic acids. The dl-alcohols (V) can be obtained by reducing the ketones represented by the formula (VI):

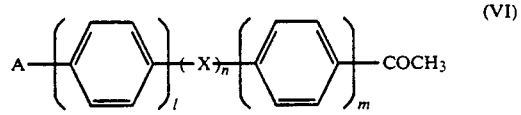

(wherein A, X, l, m and n are as defined above) by using a reducing agent.

The ketones (VI) can be easily prepared from the reactions such as shown below by chemical formulae, the proper reaction being selected according to the type of substituent X:

i) In case X is —COO— or —OCO—:
Said ketones are produced by the commonly used esterification reactions.

(Examples)

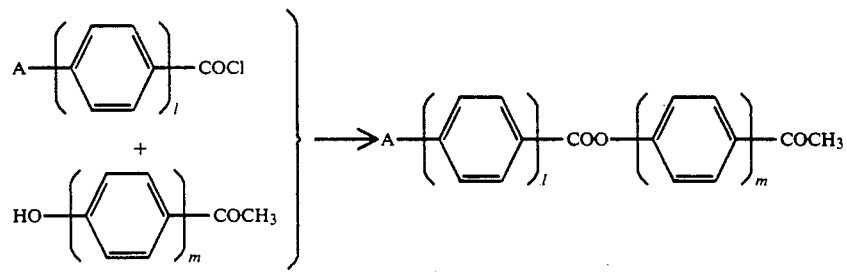

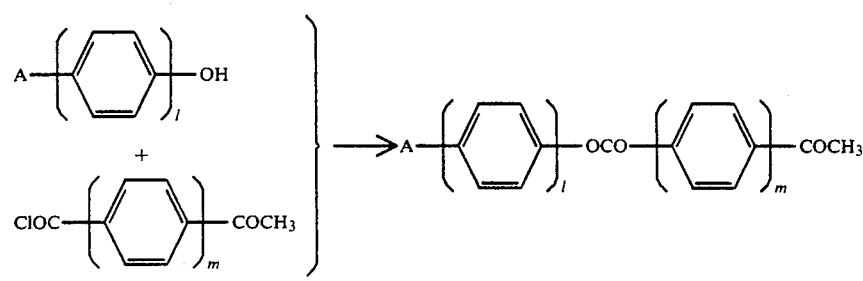

ii) In case X is —CH$_2$O— or —OCH$_2$, or n=0:
Said ketones are produced by utilizing the commonly used etherification or acylation reactions.

(Examples)

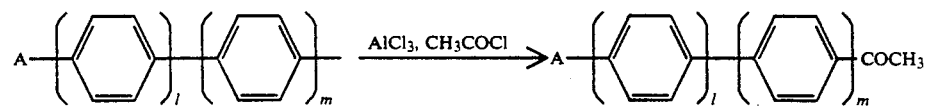

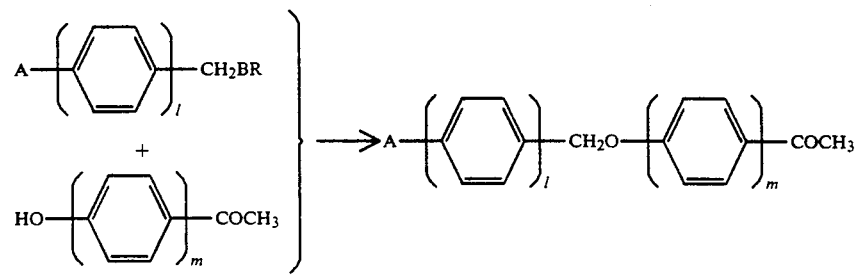

-continued
(Examples)

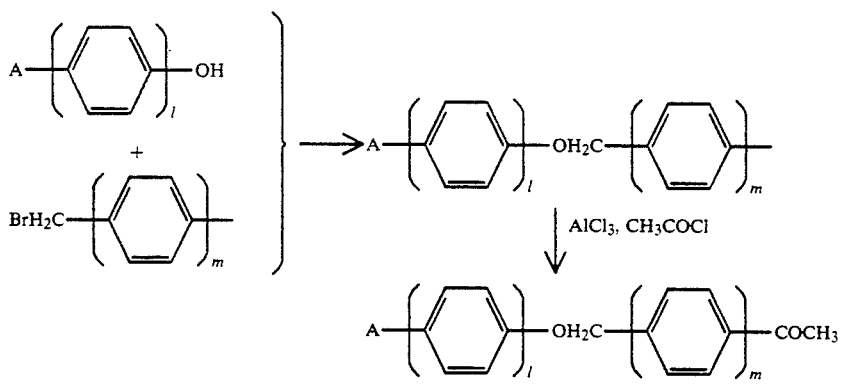

The reducing reactions for obtaining the dl-alcohols (V) from said ketones are carried out by using a reducing agent which is capable of reducing ketones into alcohols.

As the reducing agent, in case the substituent X in the starting ketones (VI) is —COO— or —OCO—, there are preferably used sodium boron hydride, lithium-tri-t-butoxyaluminum hydride, lithium-tri-s-butylboron hydride, borane and the like. In case the substituent X is —CH₂O— or —OCH₂— or n=0, sodium boron hydride, lithium boron hydride, zinc boron hydride, lithium aluminum hydride, aluminum isopropoxide, lithium-t-butoxyaluminum hydride, lithium-tri-s-butylboron hydride, borane, alkali metal-ammonia and the like are preferably used.

Such reducing agent needs to be used in an amount of at least one equivalent, usually 1 to 10 equivalents, to the starting ketone (VI).

The reducing reaction is usually carried out in a solvent. As the solvent, there can be used those which are inert to the reaction, for example, ethers such as tetrahydrofuran, dioxane, ethyl ether, etc.; alcohols such as methanol, ethanol, n-propyl alcohol, isopropyl alcohol, etc.; aromatic hydrocarbons such as benzene, toluene, etc.; halogenated hydrocarbons such as chloroform, dichloromethane, etc.; and the like. These solvents may be used either singly or in a suitable combination.

The reaction temperature may be selected from the range from −30° C. to 100° C., but the range from −20° C. to 90° C. is preferred.

The dl-alcohols (V) can be obtained in a high yield from said reaction mixtures by subjecting them to such treatments as separation, concentration, distillation and crystallization. For producing the dl-esters (IV), it is not necessary to isolate the dl-alcohols (V) but the reaction mixture may be immediately subjected to the next step.

The reaction for producing dl-esters (IV) from dl-alcohols (V) comprises reacting dl-alcohols (V) with lower alkylcarboxylic acid derivatives to acylate said alcohols.

As the lower alkylcarboxylic acid derivatives used as acylating agent in said acylation reaction, there are usually used acid anhydrides or acid halides of lower alkylcarboxylic acids, such as acetic anhydride, propionic anhydride, acetic acid chloride or bromide, propionic acid chloride or bromide, butyryl chloride or bromide, valeroyl chloride or bromide, and the like.

The reaction of dl-alcohols (V) and a lower alkylcarboxylic acid derivative is carried out under the ordinary esterification reaction conditions by using a catalyst in the presence or absence of a solvent.

In case of using a solvent in this reaction, such solvent should be the one which is inert to the reaction, for example, aliphatic or aromatic hydrocarbons, ethers, halogenated hydrocarbons and non-protonic polar solvents, such as tetrahydrofuran, ethyl ether, acetone, methyl ethyl ketone, toluene, benzene, chlorobenzene, dichloromethane, dichloroethane, chloroform, carbon tetrachloride, dimethylformamide, hexane, etc. These solvents may be used either singly or in admixture. The amount of the solvent(s) to be used in the reaction is not specified.

The amount of the lower alkylcarboxylic acid derivatives used in the reaction should be not less than one equivalent to the starting material dl-alcohol (V). Its upper threshold amount is not defined, but it is preferably four equivalents to dl-alcohol (V).

As the catalyst, there can be used organic or inorganic basic materials such as dimethylaminopyridine, triethylamine, tri-n-butylamine, pyridine, picoline, imidazole, sodium carbonate, sodium methylate, potassium hydrogencarbonate and the like. The amount of the catalyst used in the reaction, though not specified in this invention, is usually 1 to 5 equivalents to dl-alcohol (V).

When an organic amine is used as solvent, such amine may act as a catalyst as well.

Acids such as toluenesulfonic acid, methane-sulfonic acid, sulfuric acid, etc., may be used as catalyst.

The amount of the catalyst to be used can not be specified as it varies depending on the type of the lower alkylcarboxylic acid derivatives, combination thereof with the catalyst used and other factors, but in case of using an acid halide as the lower alkylcarboxylic acid derivatives, the catalyst is used in an amount of one equivalent or more to such acid halide.

The reaction temperature is usually in the range from −30° C. to 100° C., preferably −20° C. to 90° C.

The reaction time is not defined. The moment at which the starting material dl-alcohol (V) has vanished may be taken at the end point of the reaction.

The reaction is followed by the ordinary separating operations such as extraction, separation of liquid phase, concentration, recrystallization, etc., by which dl-esters (IV) can be obtained in a high yield. If necessary, the resulting product may be purified by column chromatography or other means, but the reaction mixture may be subjected in the form as it is to the treatment of the next step.

The reaction for obtaining optical active alcohols (II) from said dl-esters (IV) comprises hydrolyzing one of the optical active compounds of said dl-esters (IV) by using an esterase having the ability to hydrolyze only one of the enantiomers of said esters.

When the term "esterase" is used in this invention, it means esterases of the broad sense including lipase.

As the microorganism producing the esterase used in the above reaction, there can be employed any of those microorganisms which are capable of producing an esterase having the ability to effectuate asymmetric hydrolysis of dl-esters (IV).

Examples of such esterase-producing microorganisms are those belonging to the genera Enterobacter, Arthrobacter, Brevibacterium, Pseudomonas, Alcaligenes, Micrococcus, Chromobacterium, Microbacterium, Corynebacterium, Bacillus, Lactobacillus, Trichoderma, Candida, Saccharomyces, Rhodotorula, Cryptocccus, Torulopsis, Pichia, Penicillium, Aspergillus, Rhizopus, Mucor, Aureobasidium, Actinomucor, Nocardia, Streptomyces, Hansenula and Achromobacter.

Culture of these microorganisms is usually accomplished according to a conventional method. for example, when a liquid culture is carried out, a culture medium can be obtained in the following manner:

For instance, a sterilized liquid medium [a malt extract-yeast extract medium (prepared by dissolving 5 g of peptone, 10 g of glucose, 3 g of malt extract and 3 g of yeast extract in 1 liter of water, with pH adjusted to 6.5) for culture of mold and yeast fungi or a sweetened bouillon medium (prepared by dissolving 10 g of glucose, 5 g of peptone, 5 g of meat extract and 3 g of NaCl in 1 liter of water, with pH adjusted to 7.2) for culture of bacteria] is inoculated with microorganisms and subjected to reciprocal shaking culture usually at 20°–40° C. for 1-3 days. If necessary, solid culture may be employed.

Some of the esterases usable in the reaction of this invention are commercially available. The following can be mentioned as examples of such commercially available esterases: Lipase P (lipase derived from the Pseudomonas, available from Amano Pharmaceutical Co., Ltd.), Lipase AP (lipase derived from the Aspergillus, available from Amano Pharmaceutical Co., Ltd.), Lipase M-AP (lipase derived from the Mucor, available from Amano Pharmaceutical Co., Ltd.), Lipase MY (lipase derived from Candida Cylindlasse, available from Meito Sangyo Co., Ltd.), Lipase PL (lipase derived from the Alcaligenes, available from Meito Sangyo Co., Ltd.), Lipase AL (lipase derived from the Achromobacter, available from Metio Sangyo Co., Ltd.), Lipase Godo BSL (lipase derived from the Arthrobacter, available from Godo Shusei Co., Ltd.), lipase derived from the Chromobacterium (available from Toyo Brewage Co., Ltd.), Talipase (lipase derived from the Rhizopus Delemar, available from Tanabe Pharmaceutical Co., Ltd.), and Lipase Saiken (lipase derived from the Rhizopus, available from Osaka Bacterial Research Institute).

It is also possible to use animal and plant esterases such as steapsin, pancreatin, swine liver esterase, wheat germ esterase, etc.

Enzymes obtained from animals, plants and microorganisms can be used as esterase in the reaction of this invention, and such enzymes can be used in the various forms as desired, such as purified enzyme, crude enzyme, enzyme-containing substance, liquid culture of microorganism, culture, bacterial body, culture filtrate and their treated products. Combinations of enzymes and microorganisms are also usable. Further, fixed enzymes or fixed bacterial bodies, in which the enzymes or bacterial bodies have been fixed to a resin, etc., can be used.

The asymmetric hydrolysis reaction is carried out by vigorously stirring a mixture of the starting material dl-ester (IV) and said enzyme or microorganism usually in a buffer solution.

The buffer solution used in this reaction may be a commonly used buffer solution of an inorganic acid salt such as sodium phosphate, potassium phosphate, etc., or an organic acid salt such as sodium acetate, sodium citrate, etc. The pH of the buffer solution is preferably 8 to 11 in the case of cultures of alkaliphilic bacteria or alkaline esterases and 5 to 8 in the case of cultures of non-alkaliphilic microorganisms or esterases having no alkali resistance. The concentration of the buffer solution is usually in the range of 0.05 to 2M, preferably 0.05 to 0.5M.

The reaction temperature is usually 10 to 60° C. and the reaction time is generally 3 to 70 hours, though they are not defined in these ranges.

In case of using lipase belonging to the Pseudomonas or Arthrobacter in said asymmetric hydrolysis reaction, there can be obtained an optical active alcohol compound (II) with a relatively high optical purity.

In this hydrolysis reaction, it is also possible to use an organic solvent inert to the reaction, such as toluene, chloroform, methyl isobutyl ketone, dichloromethane, etc., in addition to the buffer solution. Use of such organic solvent allows advantageous proceeding of the asymmetric hydrolysis.

As a result of such asymmetric hydrolysis reaction, only one of the optical active substances of the starting material dl-ester (IV) is hydrolyzed to produce an optical active alcohol compound of the formula (II). On the other hand, the other optical active substance of said starting material dl-ester (IV), i.e. the optical active ester is left unhydrolyzed.

After such hydrolysis reaction has been completed, the optical active alcohol compound (II) which is the hydrolyzate and the non-hydrolyzed optical active substance of said starting ester (IV), or optical active ester, are separated by extracting the reaction solution with a solvent such as methyl isobutyl ketone, ethyl acetate, ethyl ether, etc., distilling off the solvent from the organic layer and subjecting the concentrated residue to column chromatography, or by other methods.

The optical active ester obtained here may if necessary be further hydrolyzed to be turned into an optical active alcohol compound (II) which is an enantiomer of the previously obtained optical active alcohol compound (II).

For obtaining the objective optically active benzene derivative from such optical active alcohol compound (II), said compound (II) is reacted with an aliphatic carboxylic acid.

The aliphatic carboxylic acids usable in this reaction include those listed below as well as their acid anhydrides or acid halides (such as acid chloride and acid bromide): acetic acid, propionic acid, butanoic acid, pentanoic acid, hexanoic acid, heptanoic acid, octanoic acid, nonanoic acid, decanoic acid, undecanoic acid, dodecanoic acid, tridecanoic acid, tetradecanoic acid, pentadecanoic acid, hexadacanoic acid, heptadecanoic acid, octadecanoic acid, nonadecanoic acid, eicosanic acid, isobutyric acid, 2-methylbutanoic acid, 4-methylpentanoic acid, 2-methylhexanoic acid, 2-methylheptanoic acid, 2-methyloctanoic acid, 2-methylbutanoic acid, 2,3-dimethylbutanoic acid, 2,3,3-trimethylbutanoic acid, 2-methylpentanoic acid, 3-methylpentanoic acid, 2,3-dimethylpentanoic acid, 2,4-dimethylpentanoic acid, 2,3,3,4-tetramethylpentanoic acid, 2-methylhexanoic acid, 3-methylhexanoic acid, 4-methylhexanoic acid, 2,5-dimethylhexanoic acid, 2-methylheptanoic acid, and 2-methyloctanoic acid. Among the above aliphatic carboxylic acids, those having an asymmetric carbon atom may be used even if they are either racemic or optical active compound.

Certain of these optical active carboxylic acids can be obtained by oxidizing the corresponding alcohols or by the reductive deamination of the amino acids. Some optical active aliphatic carboxylic acids exist in nature. Also, some of them can be derived from the optical active amino acids or optical active oxyacids such as listed below which exist naturally or are obtainable by resolution: alanine, valine, leucine, isoleucine, phenylalanine, serine, threonine, allothreonine, homoserine, alloisoleucine, tertleucine, 2-aminobutyric acid, norvaline, norleucine, ornithine, lysine, hydroxylysine, phenylglycine, trifluoroalanine, aspartic acid, glutamic acid, lactic acid, mandelic acid, tropic acid, 3-hydroxybutyric acid, malic acid, tartaric acid, and iso-propylmalic acid.

The reaction of optical active alcohol compound (II) and aliphatic carboxylic acid is usually carried out in the presence or absence of a solvent and generally in the presence of a catalyst.

The solvents usable in this reaction are the ones which are inert to the reaction, for example, aliphatic or aromatic hydrocarbons, esters, ethers and halogenated hydrocarbons such as tetrahydrofuran, ethyl ether, acetone, methyl ethyl ketone, ethyl acetate, toluene, benzene, chlorobenzene, dichloromethane, dichloroethane, chloroform, carbon tetrachloride, dimethylformamide and hexane, which may be used either singly or in combination. The amount of such solvent to be used in said reaction is not specifically defined.

The amount of acid anhydride or acid halide of aliphatic carboxylic acid to be used in the reaction should be not less than one equivalent to the optical active alcohol compound. Its upper threshold amount is not subject to any definite limitation, but it is preferably 4 equivalents to said alcohol compound.

As the catalyst, organic or inorganic basic materials such as dimethylaminopyridine, triethylamine, tri-n-butylamine, pyridine, picoline, imidazole, sodium carbonate, sodium methylate and potassium hydrogencarbonate can be used. Organic or inorganic acids such as toluenesulfonic acid, methanesulfonic acid, sulfuric acid, etc., are also usable as catalyst.

In case of using, for instance, an acid halide of aliphatic carboxylic acid as starting material, pyridine is most preferably used as catalyst.

The amount of the catalyst to be used in the reaction varies according to the type of acid anhydride or acid halide of aliphatic carboxylic acid used, combination thereof with the catalyst used, etc., but in case of using an acid halide, the catalyst should be used in an amount of at least one equivalent to the acid halide.

In case of using an aliphatic carboxylic acid, dehydrating-condensation is carried out by using 1 to 4 equivalents, preferably 1 to 2 equivalents of said carboxylic acid to one equivalent of the optical active alcohol compound used as starting material. As condensing reagent, there can be used carbodiimides such as N,N'-dicyclohexylcarbodiimide, N-cyclohexyl-N'-(4-diethylamino)cyclohexyl carbodiimide, etc., and if necessary an organic base such as 4-pyrrolidinopyridine, pyridine, triethylamine, etc. The amount of such condensing agent to be used in the reaction should be 1 to 1.2 equivalent to said carboxylic acid, and the amount of the base to be used should be 0.01 to 0.2 equivalent to said condensing agent.

As the solvent, those inert to the reaction such as mentioned previously can be used.

The reaction temperature is usually $-30°$ C. to $100°$ C., preferably $-25°$ C. to $80°$ C.

No particular limit is imposed on the reaction time. The moment at which the optical active alcohol compound used as starting material has vanished may be supposed to be the end point of the reaction.

After the end of the reaction, the desired optically active benzene derivative of the formula (I) can be isolated from the reaction mixture by subjecting to the ordinary separating operations such as filtration, extraction, separation of liquid phase, concentration, etc. If necessary the isolated substance may be purified by column chromatography or other means.

The optically active benzene derivatives obtainable from the above-described process include, for instance, p-(1-alkylcarbonyloxethyl)phenyl benzoate, p'-(1-alkylcarbonyloxyethyl)phenyl p-halobenzoate, p'-(1-alkylcarbonyloxyethyl)phenyl p-alkylbenzoate, p'-(1-alkylcarbonyloxyethyl)phenyl p-alkyloxybenzoate, 4'-(1-alkylcarbonyloxy ethyl)-4-biphenylyl benzoate, 4'-(1-alkylcarbonyloxyethyl)-4-biphenylyl p-halobenzoate, 4'-(1-alkylcarbonyloxyethyl)-4-biphenylyl p-alkylbenzoate, 4'-(1-alkylcarbonyloxyethyl)-4-biphenylyl p-alkyloxybenzoate p-(1-alkylcarbonyloxyethyl)phenyl 4-biphenylcarboxylate, p-(1-alkylcarbonyloxyethyl)phenyl 4'-halo-4-biphenylcarboxylate, p-(1-alkylcarbonyloxyethyl)phenyl 4-alkyl-4-biphenylcarboxylate, p-(1-alkylcarbonyloxyethyl)phenyl 4'-alkyloxy-4-biphenylcarboxylate, 4'-(1-alkylcarbonyloxyethyl)-4-biphenyl 4-biphenylcarboxylate, 4'-(1-alkylcarbonyloxyethyl)-4-biphenyl 4'-halo-4-biphenylcarboxylate, 4'-(1-alkylcarbonyloxyethyl)-4-biphenyl 4'-alkyl-4-biphenylcarboxylate, and 4'-(1-carbonyloxyethyl)-4-biphenyl 4'-alkyloxy-4-biphenylcarboxylate.

In the above-shown examples of the optical active compounds according to this invention, "alkyl" represents alkyl groups having 1 to 20 carbon atoms, such as methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, isopropyl, 1-methylpropyl, 3-methylbutyl, 1-methylpentyl, 1-methylhexyl and 1-methylheptyl. Such "alkyl" may also represent optical active alkyl groups such as 1-methylpropyl, 1,2-dimethylpropyl, 1,2,2-trimethylpropyl, 1-methylbutyl, 1,3-dimethylbutyl, 1,2,2,3-tetramethylbutyl, 1-methylpentyl, 2-methylpentyl, 3-methylpentyl, 1,3-dimethylpentyl, 1-methylhexyl, and 1-methylheptyl.

Shown above are the optically active benzene derivatives in which the bonding groups X is —COO—, but those in which the bonding group is —OCO—, —CH$_2$O— or —OCH$_2$— instead of —COO— or n=0 can be also similarly obtained from the process of this invention.

The optically active benzene derivatives provided according to this invention can be utilized as a liquid-crystalline substance, and many of such derivative present a liquid crystal phase which is either $S_A$ phase or $S_C^*$ phase.

Generally, in the liquid crystals having $S_C^*$ phase, especially ferroelectric liquid crystals, the molecules are arranged with an inclination to a specific direction and the direction of inclination shifts slightly from layer to layer to form a spiral structure in the molecular orientation (Mol. Cryst. and Liq. Cryst., 40, 30 (1977)). It is said that spontaneous polarization tends to occur at a location which is in a direction orthogonal to the axis of said spiral, and it is pointed out as the conditions for such ferro-electric liquid crystal that the crystal has an optical active group for inducing a spiral structure at the end of the molecule and that, in order to induce spontaneous polarization, the crystal has at the end of the molecule a substituent having a permanent dipole in the direction substantially vertical to the major axis of the molecule.

While the existence of an optical active group in the molecule is essential as said above, it has been considered desirable to bring the optical active group close to the core for inducing even greater spontaneous polarization (Liquid Crystals and Ordered Fluids, Vol. 4, 1-32 (1982)). But on the other hand, it has been also considered that when the optical active center comes close to the core, it becomes difficult for the compound to assume a liquid crystal phase.

Among the conventional liquid crystal compounds, however, there has been none having an asymmetric carbon atom at a position directly bonded to the core.

The optically active benzene derivatives represented by the formula (I) according to this invention can satisfy said conditions and has a quite novel molecular structure in which the optical active center is located at a position directly bonded to the core, and further it has been clarified that such compounds are capable of having very great spontaneous polarization.

In practical utilization of such liquid-crystalline materials, they can not only be provided as a mixed composition but can be also added to a ferro-electric liquid crystal having very small spontaneous polarization to provide a composition capable of having large spontaneous polarization.

In use of the compounds of the this invention, it is considered that those of the compounds of this invention which take the $S_C^*$ phase in itself have higher utility, and especially those which take such phase enantiotropically are preferred. In view of this, the compounds of the formula (I) wherein X is —OCO—, l=2 and n=1 are most favorable for practical utilization.

Even those compounds which take no $S_C^*$ phase are also useful. They may be added to an $S_C$ or $S_C^*$ phase liquid crystal having no or very small spontaneous polarization to enlarge spontaneous polarization of the liquid crystal composition to thereby increase response speed. The compounds of this invention prove advantageous in such mixing as they have high compatibility and excellent stability.

Also, the compounds of the formula (I) wherein X is —CH$_2$O, l is 1 and A is a hydrogen atom, a halogen atom, a lower alkyl or a lower alkoxyl group are useful as an intermediate. For instance, when they are subjected to catalytic hydrogenation, they are debenzylated to give benzene alcohols.

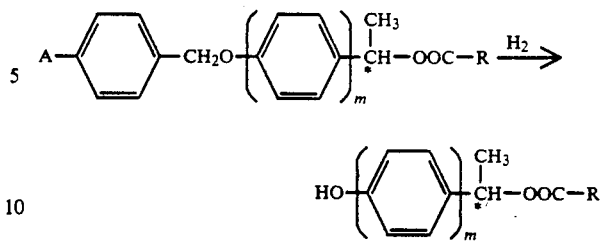

Such benzene alcohols can be led into the compounds of this invention by reacting them with benzene carboxylic acids.

As described above, the optically active benzene derivatives of this invention are useful as a liquid-crystalline material. For instance, they can be effectively utilized as a material for liquid crystal elements, optical switching elements, etc. In such practical applications, the optically active benzene derivative of this invention may be used alone or in combination with other liquid crystal compound according to the purpose of use and other factors involved. The methods for utilization are diversified.

Thus, the novel optical active benzene derivatives of this invention can be effectively utilized as a novel liquid-crystalline substance and have an extremely high industrial utility value.

DESCRIPTION OF THE PREFERRED EMBODIMENTS

The present invention will be further described below in accordance with the examples thereof.

EXAMPLE 1

Material Preparation 90.45 g (0.4 mol) of 4-benzyloxyacetophenone, 300 ml of tetrahydrofuran and 100 ml of methanol were supplied into a four-necked flask equipped with a stirrer and a thermometer. Then 15.14 g (0.4 mol) of sodium borohydride was added at 15°-25° C. over a period of 2 hours. After kept at the same temperature for 5 hours, the mixture was poured into ice-water and extracted twice with 500 ml of ethyl acetate. The organic layer was concentrated under reduced pressure to obtain 88.5 g of 4-benzyloxy-1-phenethyl alcohol in a 97% yield.

68.44 g (0.3 mol) of 4-benzyloxy-1-phenethyl alcohol was dissolved in a mixed solution of 300 ml of toluene and 50 ml of pyridine, and then 25.91 g (0.33 mol) of acetyl chloride was added at 15°-20° C. over a period of 2 hours. The mixture was kept at the same temperature for one hour and then at 40°-50° C. for 2 hours.

The reaction mixture was cooled below 10° C. and added with 200 ml of water. After separating the liquid phase, the organic layer was washed with 1N hydrochloric acid solution, water, 5% sodium carbonate and water successively in that order, then concentrated under reduced pressure and purified by column chromatography to give 79.8 g (98.5% yield) of acetic ester of 4-benzyloxy-1-phenethyl alcohol.

67.5 g (0.25 mol) of this acetic ester of 4-benzyloxy-1-phenethyl alcohol was mixed with 700 ml of 0.3M phosphate buffer solution (pH 7.5) and 6.75 g of Amano Lipase P and vigorously stirred at 40°-45° C. for 40 hours. The reaction mixture was extracted with 500 ml of ethyl acetate. The organic layer was concentrated under reduced pressure and the residue was purified by column chromatography using a 5:2 mixed solution of toluene and ethyl acetate as developing solvent to give 23.38 g (41% yield) of (+)-4-benzyloxy-1-phenethyl alcohol ($[\alpha]_D^{20} = +35.9°$ (c=1, CHCl$_3$), m.p.=66°-68° C.).

were used as starting material. The results are shown in Table 1.

TABLE 1

| Example | Starting ketone A | X | l | m | Optical active alcohol produced[1] Yield (%) | Melting point (°C.) | $[\alpha]_D^{20}$ c=1, chloroform |
|---|---|---|---|---|---|---|---|
| 3 | C$_8$H$_{17}$O | —CH$_2$O— | 1 | 2 | 44 | 158.5-160 | +21° |
| 4 | " | —OCH$_2$— | 2 | 1 | 46 | 143-144 | +24° |

[1]Substituent A, X, l and m are the same as those of the ketones used starting material.

EXAMPLE 2

Material Preparation 120.9 g (0.4 mol) of 4'-acetyl-4-benzyloxybiphenyl, 400 ml of tetrahydrofuran and 100 ml of methanol were supplied into a four-necked flask equipped with a stirrer and a thermometer. Then 15.14 g (0.4 mol) of sodium borohydride was added at 15°-25° C. over a period of 2 hours. The mixture was kept at the same temperature for 5 hours, then poured into ice-water and extracted twice with 500 ml of chloroform. The organic layer was concentrated under reduced pressure to obtain 117.4 g of 4-benzyloxy-4'-(1-hydroxyethyl)biphenyl in a 96.5% yield.

91.25 g (0.3 mol) of this 4-benzyloxy-4'-(1-hydroxyethyl)biphenyl was dissolved in a mixed solution of 400 ml of toluene and 100 ml of pyridine, and then 25.91 g (0.33 mol) of acetyl chloride was added at 15°-20° C. over a period of 2 hours. The mixture was kept at the same temperature for one hour and then at 40°-50° C. for 2 hours.

The reaction mixture was cooled below 10° C. and added with 300 ml of water. After separating the liquid phase, the organic layer was washed with 1N hydrochloric acid solution, water, 5% sodium carbonate and water successively in that order, then concentrated under reduced pressure and purified by column chromatography to give 101.57 g of acetic ester of 4-benzyloxy-4'-(1-hydroxyethyl)biphenyl in a 97.8% yield.

86.55 g (0.25 mol) of this acetic ester of 4-benzyloxy-4'-(1-hydroxyethyl)biphenyl was mixed with 2,000 ml of 0.3M phosphate buffer solution (pH 7.5), 50 ml of chloroform and 50 g of Amano Lipase P and stirred vigorously at 40°-45° C. for 120 hours. The reaction mixture was extracted with 1,000 ml of chloroform. The organic layer was concentrated under reduced pressure and the residue was purified by column chromatography using a 5:2 mixed solution of toluene and ethyl acetate to give 28.9 g of (+)-4-benzyloxy-4'-(1-hydroxyethyl)biphenyl ($[\alpha]_D^{20} = +34.8°$ (c=1, CHCl$_3$), m.p.=158°-159° C.).

EXAMPLE 3 AND 4

Material Preparation

The procedure of Material Preparation Example 1 was followed except that the ketones shown in Table 1

EXAMPLE 5

Material Preparation 40.2 g (0.1 mol) of 4'-acetyl-4-biphenyl ester of 4-pentyloxybenzoic acid, 100 ml of ethanol and 100 ml of chloroform were supplied into a four-necked flask furnished with a stirrer and a thermometer. Then 1.9 g (0.05 mol) of sodium borohydride was added at 20°-30° C. over a period of 10 minutes.

The mixture was kept at the same temperature for 3 hours, then poured into ice-water and extracted twice with 200 ml of chloroform.

The organic layer was washed with water and concentrated under reduced pressure to obtain 40.1 g of 4'-(1-hydroxyethyl)-4-biphenyl ester of 4-pentyloxybenzoic acid in a 99.1% yield.

20.2 g (0.05 mol) of said 4-pentyloxybenzoic ester was dissolved in a mixed solvent of 100 ml of pyridine and 200 ml of chloroform, and then 5.5 g (0.07 mol) of acetyl chloride was added at 10°-15° C. over a period of one hour. The mixture was kept at 40°-50° C. for 2 hours.

The resulting reaction mixture was cooled below 10° C. and added with 200 ml of water. After separating the liquid phase, the organic layer was washed with 3N hydrochloric acid, water, 7% sodium hydrogencarbonate and water successively in that order and concentrated under reduced pressure to obtain 21.6 g of 4'-(1-acetoxyethyl)-4-biphenylyl ester of 4-pentyloxybenoic acid in a 97% yield.

8.9 g (0.02 mol) of said ester of 4-pentyloxybenzoic acid was mixed with 300 ml of 0.3M phosphate buffer solution (pH 7), 20 ml of chloroform and 1.8 g of Amano Lipase P and stirred vigorously at 35°-40° C. for 24 hours.

The reaction mixture was extracted with 300 ml of chloroform. The organic layer was concentrated under reduced pressure and the residue was purified by column chromatography using a 20:1 mixed solution of chloroform and ethyl acetate as developing solvent to give 3.6 g of (+)-4'-(1-hydroxyethyl)-4-biphenylyl ester of 4-pentyloxybenzoic acid (melting point: 186°-188° C., $[\alpha]_D^{20} = +24.2°$ (c=1, chloroform).

EXAMPLES 6-12

Material Preparation

The procedure of Material Preparation Example 5 was followed except that the ketones shown in Table 2 were used as starting material. The obtained results are shown in Table 2.

TABLE 2

| Example | Starting ketone A | X | l | m | Optical active alcohol produced[1] Yield (%) | Melting point (°C.) | $[\alpha]_D^{20}$ c=1, chloroform |
|---|---|---|---|---|---|---|---|
| 6 | C$_8$H$_{17}$O | —COO— | 1 | 2 | 45 | 135-136 | +22° |
| 7 | C$_{10}$H$_{21}$O | —COO— | 1 | 2 | 46 | 138.5-140 | +20.4° |

TABLE 2-continued

| | Starting ketone | | | | Optical active alcohol produced[*1] | | |
|---|---|---|---|---|---|---|---|
| Example | A | X | l | m | Yield (%) | Melting point (°C.) | $[a]_D^{20}$ c=1, chloroform |
| 8 | $C_8H_{17}O$ | —COO— | 1 | 1 | 49 | 85–86 | +22.3° |
| 9 | $C_8H_{17}O$ | —OCO— | 1 | 1 | 45 | 134–135 | +29.1° |
| 10 | $C_5H_{11}$ | —COO— | 1 | 2 | 46 | 142–143 | +26.4° |
| 11 | $C_8H_{17}$ | —COO— | 1 | 2 | 46 | 110.5–111 | +24.1° |
| 12 | $C_8H_{17}O$ | —COO— | 2 | 1 | 45 | 149–150 | +18.3° |

[*1] Substituent A, X, l and m are the same as those of the ketones used as a starting material.

EXAMPLE 13

Material Preparation 500 ml of ethanol, 23.96 g (0.106 mol) of 4-acetyl-4'-methoxybiphenyl and 5.60 g (0.148 mol) of sodium borohydride were applied into a three-necked flask and stirred under heating at 50° C. for about 2 hours. After the reaction was completed, ethanol was distilled off under reduced pressure and the residue was extracted with diethyl ether. The ether layer was washed well with water and dried over anhydrous magnesium sulfate. The solvent was then distilled off to give a white solid.

This white solid was dissolved in 200 ml of dry dichloromethane, followed by addition of 50 ml of pyridine. Then a solution of 12.5 g (0.159 mol) of acetyl chloride in 50 ml of dichloromethane was added dropwise. About 2 hours later, the reaction solution was added into 300 ml of 3N hydrochloric acid and extracted. The organic layer was washed with water and a 7% sodium hydrogencarbonate solution successively in that order and dried over anhydrous magnesium sulfate. Then the solvent was distilled off. The resulting white solid was recrystallized from ethanol to give 20.36 g of dl-4-(1-acetoxyethyl)-4'-methoxybiphenyl in a 71% yield.

A 10 ml chloroform solution of 6.0 g (0.022 mol) of dl-4-(1-acetoxyethyl)-4'-methoxybiphenyl and 1.0 g of lipase ("Amano P" lipase made by Amono Pharmaceutical Co., Ltd.) were added into 300 ml of a 0.1M phosphate buffer solution (pH 7) and stirred vigorously under a nitrogen atmosphere at 35° C. for 29 hours for reacting said materials.

The resulting reaction solution was extracted with ethyl acetate. The extract was concentrated and purified by column chromatography using a chloroform-ethyl acetate mixture as developing solvent to give 1.9 g (43% yield) of (+)-4-(1-hydroxyethyl)-4'-methoxybiphenyl ($[a]_D^{25}$=+40.1° (c=1, chloroform), melting point: 132°–133° C.).

EXAMPLE 14

Material Preparation

The procedure of Material Preparation Example 13 was followed except that 4-acetyl-4'-octyloxybiphenyl was used as starting material to obtain (+)-4-(1-hydroxyethyl)-4'-octyloxybiphenyl ($[a]_D^{25}$=+28.6° (c=1, chloroform), melting point: 124°–125° C.).

EXAMPLE 15

4.56 g (20 mmol) of (+)-4-benzyloxy-1-phenethyl alcohol was dissolved in 50 ml of dry pyridine, and to this solution was added dropwise 1.73 g (22 mmol) of acetyl chloride. The mixture was stirred at room temperature for one hour, then poured into 400 ml of 2N hydrochloric acid and extracted with 200 ml of toluene. The toluene layer was washed with water, a 7% sodium bicarbonate solution and water successively in that order and then dried over anhydrous magnesium sulfate. The solvent was distilled off under reduced pressure from this toluene solution, and the resulting white solid was purified by column chromatography packed with 200 g of silica gel to obtain 5.35 g of acetic acid ester of (+)-4-benzyloxy-1-phenethyl alcohol in a 99% yield. It was further recrystallized from ethanol. $[a]_D^{25}$=+93° (c=1, $CHCl_3$; melting point: 52°–53° C.

EXAMPLE 16

The procedure of Example 15 was repeated but by using propionic acid chloride in place of acetyl chloride to obtain propionic acid ester of (+)-4-benzyloxy-1-phenethyl alcohol. $[a]_D^{25}$=+89° (c=1, $CHCl_3$); melting point: 48° C.

EXAMPLE 17

The procedure of Example 15 was followed except that (+)-4-(4-methylbenzyl)oxy-1-phenethyl alcohol was used in place of (+)-4-benzyloxy-1-phenethyl alcohol to obtain acetic acid ester of (+)-4-(4-methylbenzyl)oxy-1-phenethyl alcohol. $[a]_D^{25}$=+91° (c=1, $CHCl_3$); melting point: 54°–55° C.

EXAMPLE 18

In Example 15, (+)-4-benzyloxy-1-phenethyl alcohol was replaced by (+)-4-(4-methoxybenzyl)oxy-1-phenethyl alcohol and acetyl chloride was replaced by decanoyl chloride, and otherwise the same procedure as Example 15 was followed to obtain decanoic acid ester of (+)-p-(4-methoxybenzyl)oxy-1-phenethyl alcohol.

EXAMPLE 19

6.09 g (20 mmol) of (+)-4-benzyloxy-4'-(1-hydroxyethyl)biphenyl was dissolved in 100 ml of dry pyridine, followed by dropwise addition of 1.73 g (22 mmol) of acetyl chloride. The mixture was stirred at room temperature for one hour, then poured into 1 liter of 2N hydrochloric acid and extracted with 300 ml of toluene. The toluene layer was washed with water, then with a 7% sodium bicarbonate solution and again with water successively in that order and then dried over anhydrous magnesium sulfate. This toluene solution was distilled under reduced pressure to remove the solvent and the residual white solid was purified by column chromatography packed with 200 g of silica gel to obtain 6.86 g of (+)-4-benzyloxy-4'-(1-acetoxyethyl)-biphenyl in a 99% yield. It was further purified by recrystallization from ethanol. $[a]_D^{25}$=+56.3° (c=1, $CHCl_3$); melting point: 137° C.

EXAMPLE 20

The procedure of Example 19 was followed except for use of propionic acid chloride in place of acetyl chloride to obtain (+)-4-benzyloxy-4'-(1-propionyloxyethyl)biphenyl. $[\alpha]_D^{25} = +55°$ (c=1, CHCl$_3$); melting point: 125° C.

EXAMPLE 21

By using (+)-4-(p-chlorobenzyl)oxy-4'-(1-hydroxyethyl)biphenyl instead of (+)-4-benzyloxy-4'-(1-hydroxyethyl)biphenyl, the procedure of Example 19 was followed to obtain acetic acid ester of (+)-4-(p-chlorobenzyl)oxy-4'-(1-hydroxyethyl)biphenyl. $[\alpha]_D^{25} = +52°$ (c=1, CHCl$_3$); melting point: 140°–141° C.

EXAMPLE 22

4.47 g (10 mmol) of (+)-4'-(1-hydroxyethyl)-4-biphenyl ester of 4-octyloxybenzoic acid was dissolved in 100 ml of dry pyridine, and then 2.7 g (15 mmol) of octanoyl chloride was added dropwise. The mixture was stirred at room temperature for one hour, poured into 1 liter of 2N hydrochloric acid and extracted with 500 ml of toluene. The toluene layer was washed with water, a 7% sodium bicarbonate solution and water successively in that order and then dried over anhydrous magnesium sulfate. This toluene solution was distilled under reduced pressure to remove the solvent and the residual white solid was purified by column chromatography packed with 400 g of silica gel to give 5.58 g (95% yield) of (+)-4'-(1-heptylcarbonyloxyethyl)-4-biphenylyl ester of 4-octyloxybenzoic acid. This was further purified by recrystallization from ethanol. $[\alpha]_D^{25} = 49.4°$ (c=1, chloroform); phase transition temperature (°C.): K $^{78.5}$ S$_A$ $^{86.6}$ I.

EXAMPLE 23

The procedure of Example 22 was followed except that (+)-4-(1-hydroxyethyl)phenyl ester of 4-octyloxybenzoic acid was used in place of (+)-4'-(1-hydroxyethyl)-4-biphenyl ester of 4-octyloxybenzoic acid and that hexanoyl chloride was used in place of octanoyl chloride to obtain (+)-4-(1-pentylcarbonyloxyethyl)-phenyl ester of 4-octyloxybenzoic acid. $[\alpha]_D^{25} = +51°$ (c=1, CHCl$_3$); melting point: 5°–7° C.

EXAMPLE 24

The procedure of Example 23 was repeated but by using acetyl chloride in place of hexanoyl chloride to obtain (+)-4-(1-methylcarbonyloxyethyl)phenyl ester of 4-octyloxybenzoate. $[\alpha]_D^{25} = +60°$ (c=1, CHCl$_3$): melting point: 46°–47° C.

EXAMPLES 25–62

According to the process of Example 15 or 22, there were produced the optically active benzene derivatives shown in Table 3. The optical rotation and phase transition temperature of the obtained compounds are shown in Table 3.

TABLE 3

$$A-\left(\bigcirc\right)_l-(X)_n-\left(\bigcirc\right)_m-\overset{CH_3}{\underset{*}{C}}HOCOR$$

| Example | A | X | l | m | R | $[\alpha]_D^{25}$ (c=1, CHCl$_3$) | Phase transition temperature (°C.) |
|---|---|---|---|---|---|---|---|
| 25 | C$_5$H$_{11}$O | —COO— | 1 | 2 | CH$_3$ | +70° | K $\xrightarrow{87.8}$ S$_A$ $\xrightarrow{103.5}$ I |
| 26 | " | " | " | " | C$_5$H$_{11}$ | +58° | |
| 27 | " | " | " | " | C$_8$H$_{17}$ | +54° | K $\xrightarrow{78.5}$ I, S$_A$ 75 |
| 28 | " | " | " | " | C$_{17}$H$_{35}$ | +43° | K $\xrightarrow{72}$ I |
| 29 | C$_8$H$_{17}$O | " | " | " | CH$_3$ | +57° | K $\xrightarrow{91.4}$ S$_A$ $\xrightarrow{105.5}$ I |
| 30 | " | " | " | " | C$_3$H$_7$ | +61° | K $\xrightarrow{74.5}$ S$_A$ $\xrightarrow{94.5}$ I, S$_{C^*}$ 65 |
| 31 | " | " | " | " | C$_5$H$_{11}$ | +56° | K $\xrightarrow{78}$ S$_A$ $\xrightarrow{91}$ I |
| 32 | C$_8$H$_{17}$O | —COO— | 1 | 2 | C$_9$H$_{19}$ | +52° | K $\xrightarrow{74}$ S$_A$ $\xrightarrow{89}$ I |
| 33 | C$_{10}$H$_{21}$O— | " | " | " | —CH$_3$ | +60° | K $\xrightarrow{88}$ S$_A$ $\xrightarrow{103}$ S$_1$ $\xrightarrow{104}$ I |
| 34 | " | " | " | " | —C$_3$H$_7$ | +58° | K $\xrightarrow{77}$ S$_A$ $\xrightarrow{92}$ I, 55.4 C* 77 |
| 35 | " | " | " | " | —C$_5$H$_{11}$ | +52° | K $\xrightarrow{82}$ S$_A$ $\xrightarrow{88}$ I, 80, S$_{C^*}$ $\xrightarrow{61}$ S$_{H^*}$ |

TABLE 3-continued $$A-\left(\underset{l}{\underbrace{\bigcirc}}\right)-(X)_n-\left(\underset{m}{\underbrace{\bigcirc}}\right)-\overset{CH_3}{\underset{*}{C}HOCOR}$$

| Example | A | X | l | m | R | $[\alpha]_D^{25}$ (c=1, CHCl$_3$) | Phase transition temperature (°C.) |
|---|---|---|---|---|---|---|---|
| 36 | " | " | " | " | —C$_8$H$_{17}$ | +48° | K $\xrightarrow{82}$ S$_A$ $\xrightarrow{84}$ I ; S$_H^*$ 82 |
| 37 | C$_{16}$H$_{33}$O— | " | " | " | —CH$_3$ | +45° | K $\xrightarrow{87}$ S$_A$ $\xrightarrow{101}$ I |
| 38 | C$_5$H$_{11}$— | —COO— | 1 | 2 | —C$_8$H$_{17}$ | +56° | K $\xrightarrow{53}$ S$_A$ $\xrightarrow{56}$ I |
| 39 | C$_8$H$_{17}$— | " | " | " | —C$_5$H$_{11}$ | +54° | K $\xrightarrow{42}$ S$_A$ $\xrightarrow{73}$ I |
| 40 | C$_8$H$_{17}$O— | " | 2 | 1 | —CH$_3$ | +45° | K $\xrightarrow{81}$ S$_A$ $\xrightarrow{147}$ I |
| 41 | " | " | " | " | —C$_5$H$_{11}$ | +44° | K $\xrightarrow{87}$ S$_A$ $\xrightarrow{122}$ I |
| 42 | " | " | " | " | —C$_9$H$_{19}$ | +39° | K $\xrightarrow{82}$ S$_A$ $\xrightarrow{120}$ I |
| 43 | " | " | " | " | —C$_{17}$H$_{35}$ | +27° | K $\xrightarrow{83}$ S$_A$ $\xrightarrow{107}$ I |
| 44 | " | —OCO— | 1 | 1 | —C$_5$H$_{11}$ | +56° | |
| 45 | C$_{10}$H$_{21}$O— | —OCO— | 1 | 1 | —C$_9$H$_{19}$ | +46° | |
| 46 | C$_8$H$_{17}$O— | " | " | 2 | —C$_5$H$_{11}$ | +55° | K $\xrightarrow{79}$ I ; 71 ∖ S$_1$ ∕ 79 |
| 47 | C$_{10}$H$_{21}$O— | " | " | " | —C$_3$H$_7$ | +54° | K $\xleftarrow{74}$ S$_1$ $\xleftarrow{84}$ I |
| 48 | " | " | " | " | —C$_5$H$_{11}$ | +53° | K $\xrightarrow{84}$ I ; 72 ∖ S$_1$ ∕ 81 |
| 49 | " | " | " | " | —CH(CH$_3$)—C$_2$H$_5$ (S) | +40° | K — S$_1$ $\xleftarrow{57.5}$ Ch $\xleftarrow{69}$ I |
| 50 | C$_{16}$H$_{33}$O— | " | " | " | —C$_5$H$_{11}$ | +42° | K $\xleftarrow{76}$ S$_1$ $\xleftarrow{82}$ I |
| 51 | C$_8$H$_{17}$O— | —OCO— | 2 | 1 | —C$_3$H$_7$ | +60° | K $\xrightarrow{94}$ S$_C^*$ $\xrightarrow{107}$ I |
| 52 | " | " | " | " | —C$_5$H$_{11}$ | +57° | K $\xrightarrow{94}$ S$_C^*$ $\xrightarrow{101}$ I ; S$_I^*$ 88 |
| 53 | " | " | " | " | —C$_9$H$_{19}$ | +50° | K $\xrightarrow{88}$ S$_C^*$ $\xrightarrow{93}$ I |
| 54 | " | " | " | " | —C$_{17}$H$_{35}$ | +40° | K $\xrightarrow{80}$ S$_C^*$ $\xrightarrow{90}$ I |
| 55 | " | " | " | " | —CH(CH$_3$)—C$_2$H$_5$ (S) | +41° | K $\xrightarrow{86}$ S$_1$ $\xrightarrow{90}$ S$_x^*$ $\xrightarrow{93}$ Ch $\xrightarrow{102}$ I |
| 56 | C$_{10}$H$_{21}$O— | " | " | " | —C$_3$H$_7$ | +53° | K $\xrightarrow{90}$ S$_C^*$ $\xrightarrow{101}$ I |
| 57 | C$_{10}$H$_{21}$O— | —OCO— | 2 | 1 | —CH(CH$_3$)—C$_2$H$_5$ (S) | +40° | K $\xleftarrow{54}$ S$_x^*$ $\xleftarrow{87}$ Ch $\xleftarrow{93}$ I |
| 58 | C$_{12}$H$_{25}$O— | " | " | " | —C$_3$H$_7$ | +51° | K $\xrightarrow{85}$ S$_1$ $\xrightarrow{91}$ S$_C^*$ $\xrightarrow{101}$ I |

TABLE 3-continued $$A-\left(\bigcirc\right)_l-(X)_n-\left(\bigcirc\right)_m-\overset{CH_3}{\underset{*}{C}}HOCOR$$

| Example | A | X | l | m | R | $[\alpha]_D^{25}$ (c=1, CHCl₃) | Phase transition temperature (°C.) |
|---|---|---|---|---|---|---|---|
| 59 | C₆H₁₃O— | " | " | " | —C₅H₁₁ | +58° | |
| 60 | C₇H₁₅— | " | " | " | " | +55° | |
| 61 | C₁₀H₂₁— | " | " | " | —C₃H₇ | +53° | K —56→ S_A —91→ I |
| 62 | C₁₂H₂₅— | " | " | " | " | +50° | |

S₁ indicates unidentified smectic phase.
S_x* indicates unidentified ferroelectronic smectic phase.
S_x indicates unidentified smectic phase.

EXAMPLE 63

2.0 g (4.6 mmol) of (+)-4-(p-octyloxy)benzyloxy-4'-(1-hydroxyethyl)biphenyl was dissolved in 20 ml of pyridine, followed by addition of 0.9 g (5.5 mmol) of octanoyl chloride. The mixture was stirred at 40°-45° C. for one hour, then poured into 400 ml of 3N hydrochloric acid and extracted with 300 ml of toluene. The toluene layer was washed with water, then with a 7% sodium bicarbonate solution and again with water and then dried over anhydrous magnesium sulfate. The solvent was distilled off under reduced pressure from the organic layer and the resulting light-yellow solid was purified by silica gel column chromatography to obtain 2.4 g (96% yield) of (+)-4-(p-octyloxy)benzyloxy-4'-(1-octanoyloxyethyl)biphenyl. $[\alpha]_D^{25}$ = +47° (c=1, CHCl₃).

EXAMPLES 64-67 AND 76 AND 77

By following the process of Example 63, there were produced the optical active benzene derivatives shown in Table 4.

The property values of the obtained compounds are shown in Table 4.

TABLE 4

| Example | A | X | l | m | R | $[\alpha]_D^{25}$ (c=1, CHCl₃) |
|---|---|---|---|---|---|---|
| 64 | C₁₆H₃₃O | —CH₂O— | 1 | 2 | C₇H₁₅ | +36° |
| 65 | C₈H₁₇O | —OCH₂— | 1 | 2 | C₅H₁₁ | +53° |
| 66 | C₁₀H₂₁O | " | 2 | 1 | C₃H₇ | +56° |
| 67 | C₁₀H₂₁ | " | " | " | " | +50° |
| 76 | C₈H₁₇O | —CH₂O— | 1 | 2 | CH₃ | +68° |
| 77 | " | " | 1 | 2 | C₅H₁₁ | +58° |

EXAMPLE 68

2.75 g (12 mmol) of (+)-4-(1-hydroxyethyl)-4'-methoxybiphenyl was dissolved in a mixed solution of 100 ml of toluene and 20 ml of pyridine in four-necked flask provided with a stirrer and a thermometer. Then 3.52 g (20 mmol) of nonanoyl chloride was added to the solution at 15°-20° C.

The mixed solution was kept at the same temperature for one hour and then at 40°-50° C. for 2 hours.

The reaction mixture was cooled below 10° C. and added with 200 ml of water. After separating the liquid phase, the organic layer was washed with a 2N hydrochloric acid solution, water, a 5% sodium bicarbonate solution and water in that order successively.

The organic layer was concentrated under reduced pressure and purified by column chromatography to obtain 4.3 g (97% yield) of (+)-4-(1-nonanoyloxyethyl)-4'-methoxybiphenyl. $[\alpha]_D^{25}$ = +73° (c=1, chloroform); melting point: 59°-60° C.

EXAMPLES 69 and 70

The procedure of Example 68 was followed except for use of the reactants shown in Table 5.

The results are shown in Table 5.

EXAMPLE 71

38.5 g of 4"-acetyl-4-octylterphenyl, 500 ml of ethanol and 5.67 g of sodium boron hydride were supplied into a four-necked flask and stirred at 50° C. for 2 hours.

After the reaction was complete, ethanol was distilled off under reduced pressure and the residue was extracted with toluene. The organic layer was washed with water and dried over anhydrous magnesium sulfate. The solvent was then distilled off to give dl-4"-(1-hydroxyethyl)-4-octylterphenyl as a white solid.

19.3 g of this white solid was dissolved in 200 ml of dry dichloromethane, to which 20 ml of pyridine was added and then a solution of 4.7 g of acetyl chloride in 50 ml of dichloromethane was added dropwise at room temperature. About 2 hours later, the reaction solution was poured into 200 ml of 3N hydrochloric acid and extracted. The organic layer was washed with water and then with a 7% sodium hydrogencarbonate solution successively and thereafter dried over anhydrous magnesium sulfate.

The solvent was distilled off and the resulting white solid was recrystallized from ethanol to give 18.0 g of dl-4"-(1-acetoxyethyl)-4-octylterphenyl in an 84% yield.

A solution of 6.0 g of dl-4"-(1-acetoxyethyl)-4-octylterphenyl in 10 ml of chloroform and 1.0 g of lipase ("Amano P" lipase made by Amono Pharmaceutical Co., Ltd.) were added into 300 ml of a 0.1M phosphate buffer solution (pH 7) and stirred vigorously at 35° C. for 29 hours under nitrogen atmosphere.

The reaction solution was extracted with ethyl acetate. The extract was concentrated and purified by column chromatography using a chloroform-ethyl acetate mixed solvent to obtain 1.8 g (41% yield) of (+)-4"-(1-hydroxyethyl)-4-octylterphenyl. $[\alpha]_D^{25}$ = +23.6° (c=1, chloroform); 98% ee; melting point: 242° C. (decomposed).

3.86 g (10 mmol) of (+)-4‴-(1-hydroxyethyl)-4-octylterphenyl was dissolved in a mixed solution of 50 ml of toluene and 50 ml of pyridine, and then 1.9 g (12 mmol) of octanoyl chloride was added at 30°-35° C. The mixture was kept at 40°-50° C. for 2 hours.

After the reaction was completed, 200 ml of water and 200 ml of toluene were added to the reaction solution. Then the liquid phase was separated and the organic layer was washed with a 3N hydrochloric acid solution, water, a 5% sodium bicarbonate solution and water in that order successively.

The organic layer was concentrated under reduced pressure and purified by column chromatography to obtain 5.0 g (98% yield) of (+)-4-(1-octanoyloxyethyl)-4″-octylterphenyl. $[\alpha]_D^{25} = +62°$.

EXAMPLE 72

The procedure of Example 71 was followed except for the replacement of 4″-acetyl-4-octylterphenyl with 4″-acetyl-4-pentylterphenyl to obtain dl-4‴-(1-acetoxyethyl)-4-pentylterphenyl. This was further treated according to Example 71 to obtain the results shown in Table 5.

TABLE 5

| | | | | | Objective compound | | |
| Example | A | X | l | m | Acylating reagent | R | Optical rotation* | Yield (%) |
|---|---|---|---|---|---|---|---|---|
| 69 | $C_5H_{11}O-$ | —** | 1 | 1 | $C_8H_{17}COCl$ | $-C_8H_{17}CO$ | +68° | 98 |
| 70 | $C_8H_{17}O-$ | —** | 1 | 1 | " | " | +65° | 98 |
| 72 | $C_5H_{11}-$ | —** | 2 | 1 | " | " | +63° | 97 |

*c=1, chloroform
**n=0

EXAMPLE 73

The procedure of Example 15 was followed except that hexanoyl chloride was used in place of acetyl chloride to obtain hexanoic ester of (+)-p-benzyloxy-1-phenethyl alcohol. $[\alpha]_D^{25} = +73°$ (c=1, CHCl$_3$); $n_D^{25}$: 1.5289.

EXAMPLE 74

The procedure of Example 19 was followed except that octanoyl chloride was used in place of acetyl chloride to obtain (+)-4-benzyloxy-4'-(1-octanoyloxyethyl)biphenyl. $[\alpha]_D^{25} = +43°$ (c=1, CHCl$_3$); melting point: 91°-92° C.

In Table 6 below are shown the measured values of spontaneous polarization of the compounds which presented an Sc* phase. The measured values shown are those determined at a temperature 10° C. below the upper phase transition temperature of Sc*. The measured values of spontaneous polarization of these compounds were all above 100 nC/cm$^2$, and especially that of the compound of Example 30 was over 200 nC/cm$^2$.

TABLE 6

| Optically active benzene derivatives (I) (Example No.) | Spontaneous polarization (nC/cm$^2$) |
|---|---|
| 30 | 208 |
| 34 | 165 |
| 35 | 170 |
| 52 | 150 |
| 56 | 173 |
| 58 | 131 |

EXAMPLE 75

Application

The following three liquid crystal compounds were mixed in the specified molar ratios by heating and melting them to prepare a liquid crystal composition.

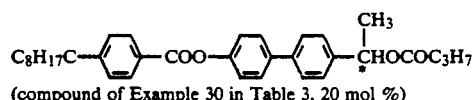

(compound of Example 30 in Table 3, 20 mol %)

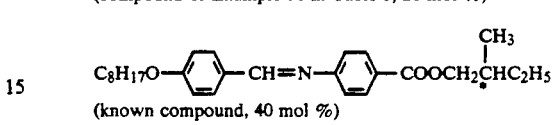

(known compound, 40 mol %)

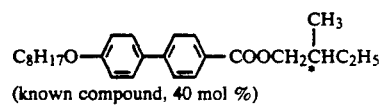

(known compound, 40 mol %)

This liquid crystal composition presented a chiral smectic (Sc*) phase at temperatures below 38° C. and showed spontaneous polarization of 40 nC/cm$^2$ at 25° C.

On the other hand, the equimolar mixture of the above two known compounds presented an Sc* phase at temperatures below 35° C. and showed spontaneous polarization of only 4 nC/cm$^2$. It was thus clarified that the use of the compounds of this invention can realize a hike of the upper limit of the temperature range in which a chiral smectic phase appears in the known compounds and an enlargement of spontaneous polarization.

Production of Liquid Crystal Element

Two glass substrates provided with transparent indium oxide electrodes were coated with a polyimide high-molecular film and lapped with a gauze in a given direction. A liquid crystal cell was assembled therewith by using glass fibers (6 μm in diameter) as spacer so that the lapping directions on the two substrates would become parallel to each other, and said liquid crystal composition was vacuum-encapsulated therein to form a liquid crystal element.

This liquid crystal element was disposed between two polarizers arranged to cross each other at right angles and an electric field was applied thereto. A change of intensity of transmitted light was observed on application of 20 V.

The response time as determined from such change of intensity of transmitted light was about 0.5 ms, and the contrast was 1:20.

The compounds of this invention which presented no Sc* phase (see Table 7 below) were combined with said known compounds to prepare the compositions in the same way as in said Application Example 75 and their spontaneous polarization was measured. Shown in Table 7 are the values of spontaneous polarization of the compositions made by blending said compounds of this invention in an amount of 20% by mole with the two know compounds (base liquid crystal). These results show that the compounds of this invention which present no Sc* phase by themselves are also effective for enlarging spontaneous polarization ($P_S$) of their mixed compositions with known compounds. It was also ascertained that the compound of Example 23, which is a bicyclic compound, could provide a large value of spontaneous polarization.

TABLE 7

| Blend | $P_S$ (nC/cm$^2$) |
| --- | --- |
| Compound of Example 29 | 26 |
| Compound of Example 26 | 28 |
| Compound of Example 41 | 32 |
| Compound of Example 46 | 39 |

TABLE 7-continued

| Blend | $P_S$ (nC/cm$^2$) |
| --- | --- |
| Compound of Example 31 | 33 |
| Compound of Example 23 | 25 |

What is claimed is:

1. An optically active alcohol compound represented by the formula:

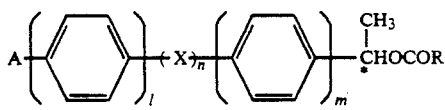

wherein X is —COO—, —OCO—, —CH$_2$O— or OCH$_2$; A is alkyl or alkoxy having 1 to 20 carbon atoms; l and m each are a number of 1 or 2; n is 1; and * indicates an asymmetric carbon atom, further provided that when X is —CH$_2$O—, A is alkyl or alkoxy having 5 to 20 carbon atoms.

* * * * *

UNITED STATES PATENT AND TRADEMARK OFFICE
CERTIFICATE OF CORRECTION

PATENT NO. : 5,274,168

DATED : DECEMBER 28, 1993

INVENTOR(S) : TAKAYUKI HIGASHII ET AL.

It is certified that error appears in the above-identified patent and that said Letters Patent is hereby corrected as shown below:

Column 26,
CLAIM 1, LINE 3, CHANGE THE FORMULA FROM

" 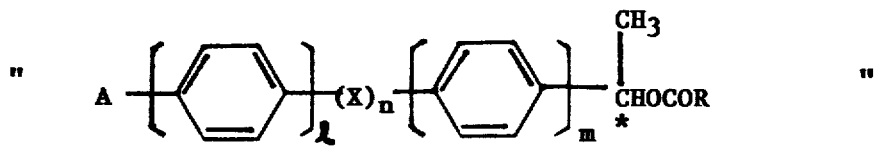 "

TO

— 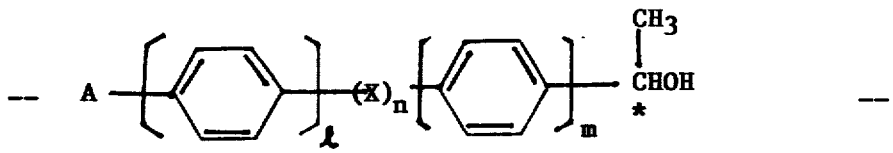 —

Signed and Sealed this

Twenty-eighth Day of June, 1994

Attest:

BRUCE LEHMAN

*Attesting Officer*  *Commissioner of Patents and Trademarks*